United States Patent [19]

Zarrabian

[11] Patent Number: 5,610,561
[45] Date of Patent: Mar. 11, 1997

[54] CRYSTAL OSCILLATOR AND BACK-UP CIRCUIT WITH OVERSPEED AND UNDERSPEED DETECTION

[75] Inventor: Morteza Zarrabian, Mountain View, Calif.

[73] Assignee: Ventritex, Inc., Sunnyvale, Calif.

[21] Appl. No.: 516,909

[22] Filed: Aug. 18, 1995

[51] Int. Cl.$^6$ ........................................... H03B 1/00
[52] U.S. Cl. .................................. 331/49; 327/292
[58] Field of Search .................... 331/49; 327/292

[56] References Cited

U.S. PATENT DOCUMENTS

| | | | |
|---|---|---|---|
| 4,485,818 | 12/1984 | Leckrone et al. | 128/419 PG |
| 4,667,328 | 5/1987 | Imran | 371/61 |
| 4,816,776 | 3/1989 | Kessler | 331/49 |

*Primary Examiner*—Siegfried H. Grimm
*Attorney, Agent, or Firm*—Steven M. Mitchell; Mark J. Meltzer

[57] ABSTRACT

A fail-safe clock generator which has particular utility in implantable cardiac defibrillators includes a crystal oscillator for generating a crystal clock signal, a back-up circuit, and a one-shot generator. The back-up circuit includes a low frequency oscillator for generating a low frequency clock signal having a frequency less than that of the crystal clock signal, and an overspeed/underspeed detector responsive to the low frequency clock signal for detecting the frequency of the crystal clock signal during each period of the low frequency clock signal, and for generating a back-up mode control signal in response to detection of either an overspeed or underspeed failure mode over a plurality of consecutive periods of the low frequency clock signal. The one-shot generator is responsive to the crystal clock signal, during a normal mode of operation, for generating an output clock signal, and is responsive to the back-up mode control signal, during a back-up mode of operation, for generating the output clock signal, e.g., in a self-clocking mode of operation.

27 Claims, 6 Drawing Sheets

5,610,561

CRYSTAL OSCILLATOR AND BACK-UP CIRCUIT WITH OVERSPEED AND UNDERSPEED DETECTION

FIELD OF THE INVENTION

The present invention relates generally to crystal oscillators, and, more particularly, to a back-up circuit for a crystal oscillator which detects an overspeed/underspeed malfunction of the crystal oscillator, and which takes over for the crystal oscillator when a detected malfunction occurs for greater than a prescribed time period. The present invention has particular utility in implantable cardiac defibrillators.

BACKGROUND OF THE INVENTION

Implantable cardiac defibrillators (ICDs) are highly sophisticated medical devices which are surgically implanted (abdominally or pectorally) in a patient to monitor the performance of the patient's heart, and to deliver electrical shocks to the patient's heart as required to correct cardiac arrhythmias which occur due to disturbances in the normal pattern of electrical conduction within the heart muscle. Cardiac arrhythmias can be thought of as disturbances of the normal rhythm of the heart beat. ICDs monitor the performance of the patient's heart by analyzing electrical signals generated by one or more sensing electrodes which are typically positioned in the right ventricular apex of the patient's heart.

In this regard, an ICD continuously monitors the heart activity of the patient in whom the device is implanted, and delivers the appropriate electrical shocks to the heart on an intermittent basis, as required, to correct detected arrhythmias, ideally before they develop into a full-blown episode of ventricular fibrillation. The waveforms and timing of these corrective (defibrillating) signals must be precisely controlled in order for the ICD to properly perform its life-saving functions (e.g., pacemaking and defibrillation). Thus, it can be appreciated that the resolution and accuracy of the timing circuits employed in ICDs is critical to the safety and reliability thereof, and thus, to the life of the patients in whom these devices are implanted. In this connection, the output frequency of the crystal oscillators utilized in ICDs must be maintained within a very narrow operating range in order to prevent device malfunction, which can have catastrophic consequences.

In this connection, presently available ICDs incorporate circuitry to detect a failure mode of a crystal oscillator in which the output frequency falls below a prescribed minimum output frequency, and to switch to a back-up clock signal generator when such a failure mode is detected. This failure mode is sometimes referred to as "underspeed" failure. However, this underspeed detection circuitry is prone to making false or erroneous detections of underspeed failure. In addition to this significant drawback, such circuitry is incapable of detecting a failure mode in which the output frequency of the crystal oscillator exceeds a prescribed maximum output frequency. This failure mode is sometimes referred to as an "overspeed" failure. This constitutes a significant shortcoming of the presently available technology.

Based on the above and foregoing, it can be appreciated that there presently exists a need in the art for a crystal oscillator back-up circuit which overcomes the above-described drawbacks and shortcomings of the presently available technology. The present invention fulfills this need.

SUMMARY OF THE INVENTION

The present invention encompasses a fail-safe clock generator which has particular utility in implantable cardiac defibrillators, and which includes a crystal oscillator for generating a crystal clock signal, a back-up circuit, and a one-shot generator. The back-up circuit includes a low frequency oscillator for generating a low frequency clock signal having a frequency less than that of the crystal clock signal, and an overspeed/underspeed detector responsive to the low frequency clock signal for detecting the frequency of the crystal clock signal during each period of the low frequency clock signal, and for generating a back-up mode control signal in response to detection of either an overspeed or underspeed failure mode over a plurality of consecutive periods of the low frequency clock signal. The one-shot generator is responsive to the crystal clock signal, during a normal mode of operation, for generating an output clock signal, and is responsive to the back-up mode control signal, during a back-up mode of operation, for generating the output clock signal, e.g., in a self-clocking mode of operation. In the following detailed description, the output clock signal during a normal mode of operation is referred to as the "crystal output clock signal", and the output clock signal during a back-up mode of operation is referred to as the "back-up clock signal".

BRIEF DESCRIPTION OF THE DRAWINGS

These and various other features and advantages of the present invention will be readily understood with reference to the following detailed description taken in conjunction with the accompanying drawings, in which.

DETAILED DESCRIPTION OF THE INVENTION

The basic design and operation of the present invention will be explained in conjunction with FIG. 1, which is a block diagram of a crystal oscillator and back-up circuit which embodies the present invention. A specific implementation of the crystal oscillator and back-up circuit which constitutes a presently preferred embodiment of the present invention will be subsequently described in conjunction with FIGS. 2–5. In this connection, although the present invention is described herein in terms of using a "crystal" oscillator, is should be clearly understood that the present invention is not limited thereto, as any other suitable type of "primary" oscillator could be employed in lieu thereof in the practice of the present invention.

Figure 1:
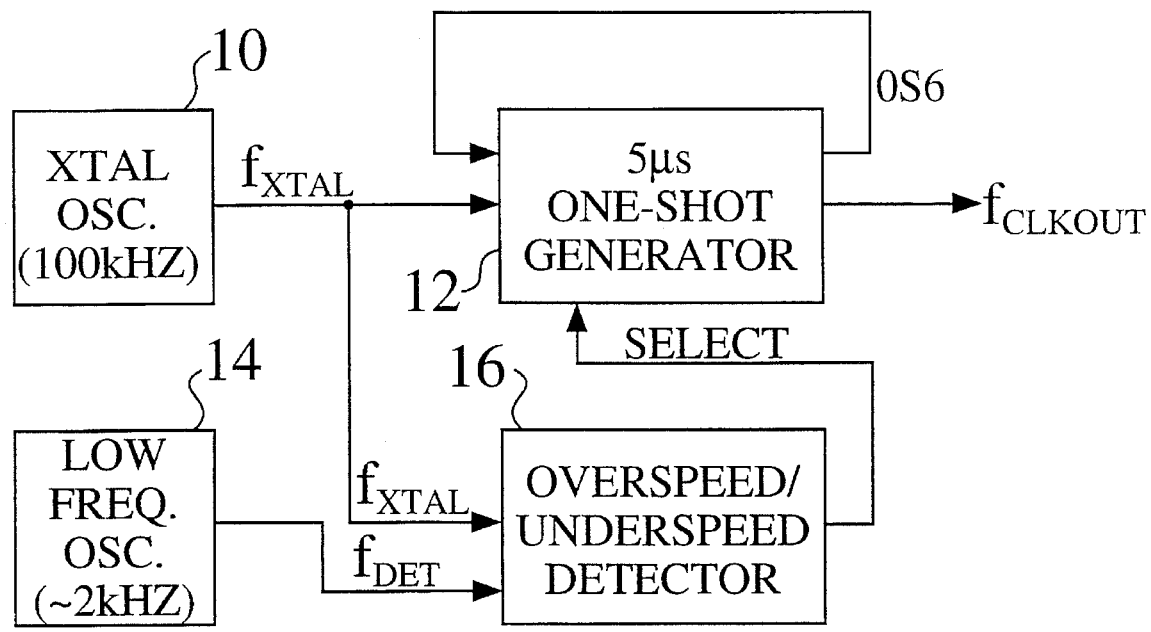
FIG. 1 is a block diagram of a fail-safe clock generator constructed in accordance with the principles of the present invention.

With reference now to FIG. 1, the crystal oscillator and back-up circuit of the present invention depicted therein includes a crystal oscillator 10, a one-shot generator 12, a low frequency oscillator 14, and an overspeed/underspeed detector 16, connected and configured as shown. In overview, the present invention works as follows. Namely, in a normal mode of operation, in which the output ($f_{XTD}$) of the crystal oscillator 10 (hereinafter referred to as "the crystal clock signal $f_{XTL}$") is within its normal operating frequency range, the one-shot generator 12 is responsive to the crystal clock signal $f_{XTL}$ to generate an output clock signal ($f_{CLKOUT}$) which is synchronized to the crystal clock signal $f_{XTL}$, and is thus referred to as a crystal output clock signal. If the overspeed/underspeed detector 16 detects that the frequency of the crystal clock signal $f_{XTL}$ either exceeds a prescribed maximum frequency for a prescribed duration (i.e., "overspeed failure"), or falls below a prescribed minimum frequency for a prescribed duration (i.e., "underspeed failure"), the detector 16 produces an output control signal ("Select") which initiates a back-up mode of operation, in which the trigger input of the one-shot generator 12 is switched from the crystal clock signal $f_{XTL}$, to the output ("OS6") of the one-shot generator 12 itself (i.e., a self-clocking mode), whereby the output clock signal $f_{CLKOUT}$ has a frequency within the normal operating frequency range of the crystal oscillator 10. The output clock signal $f_{CLKOUT}$, during the back-up mode of operation, is referred to as the "back-up output clock signal". Thus, the crystal oscillator and back-up circuit of the present invention depicted in FIG. 1 can be viewed as a high-precision, fail-safe clock generator.

More particularly, the overspeed/underspeed detector 16 is responsive to the output $f_{det}$ of the low frequency oscillator 14 (hereinafter referred to as "the low frequency $f_{det}$"), to detect or check for overspeed/underspeed failures of the crystal oscillator 10. Preferably, the frequency with which the detector 16 checks the frequency or period of the crystal clock signal $f_{XTL}$, i.e., the frequency of the low frequency clock signal $f_{det}$, is high enough to ensure a high safety margin with respect to detection of overspeed/underspeed failure of the crystal oscillator 10, but low enough to minimize erroneous detection of overspeed/underspeed failure of the crystal oscillator 10.

In the presently preferred embodiment of the present invention discussed in detail hereinafter, the frequency of the low frequency clock signal $f_{det}$ is 2 kHz, so that the period ($\tau_x$) of the crystal clock signal $f_{XTL}$ is checked by the detector 16 every 0.5 milliseconds (ms). A typical crystal oscillator used in ICDs has an output frequency of 100 kHz, with a duty cycle of 50% (trimmable), which must be maintained within a prescribed normal or safe operating range of 91 kHz-110 kHz, i.e., the period $\tau_x$ of the crystal clock signal fx must be kept within the range of 9 μs-11 μs.

If the overspeed/underspeed detector 16 detects that the crystal clock signal $f_{XTL}$ falls outside of the prescribed safe operating range a prescribed number ($\geq 1$) of consecutive times (i.e., over a prescribed number of consecutive cycles of $f_{det}$), then the detector 16 generates an output control signal which triggers the one-shot generator 12. Thus, the low frequency clock signal oscillator 14 and the overspeed/underspeed detector 16 function as a back-up circuit to the crystal oscillator 10, so that when a crystal failure mode is detected (e.g., a prescribed number of detected consecutive overspeed/underspeed failures of the crystal oscillator 10), a back-up mode of operation is initiated, in which the detector 16 takes over control of the one-shot generator 12, i.e., the trigger input of the one-shot generator 12 is switched from the crystal clock signal $f_{XTL}$ to its own output OS6. Normal operation is resumed when recovery of the crystal oscillator 10 is detected by the detector 16, i.e., the trigger input of the one-shot generator 12 is switched from OS6 to the crystal clock signal $f_{XTL}$, upon detection of the crystal clock signal $f_{XTL}$ falling within its prescribed safe operating range. Alternatively, normal operation can be resumed only after the detector 16 detects that the crystal clock signal $f_{XTL}$ has stayed within its prescribed safe (normal) operating range over a prescribed number (e.g., 4) of consecutive cycles of $f_{det}$.

In the presently preferred embodiment of the present invention discussed in detail hereinafter, the detector 16 is configured to generate the output control signal "Select" upon detection of four (4) consecutive crystal oscillator overspeed/underspeed failures, with the result that the maximum time required for the back-up circuit to take over operation of the one-shot generator 12 upon failure of the crystal oscillator 10 is 2 ms (4×0.5 ms), and the maximum time required for the crystal oscillator 10 to take over operation of the one-shot generator 12 after recovery of the crystal oscillator 10 (following an overspeed/underspeed failure thereof) is 0.5 ms.

Figure 2:
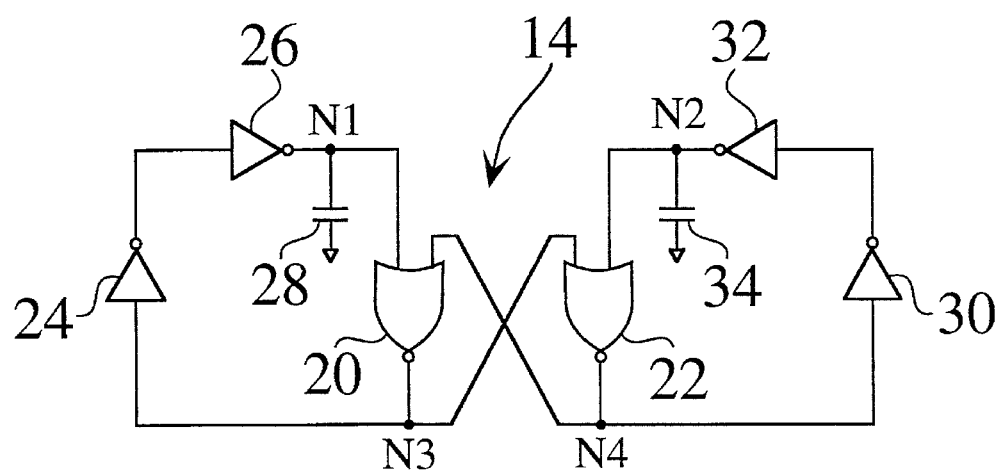
FIG. 2 is a schematic diagram of a presently preferred embodiment of the low frequency oscillator of the fail-safe clock generator of the present invention depicted in FIG. 1.

With particular reference now to FIG. 2, in a presently preferred embodiment of the present invention, the low frequency oscillator 14 is implemented as shown. More particularly, the low frequency oscillator 14 includes a latch comprised of a pair of cross-coupled NOR gates 20, 22. The output of the NOR gate 20 is fed back to its input through a feedback loop comprised of a pair of inverters 24, 26, and a capacitor 28 coupled between a node N1 and ground. The output of the NOR gate 22 is fed back to its input through a feedback loop comprised of a pair of inverters 30, 32, and a capacitor 34 coupled between a node N2 and ground. The low frequency clock signal $f_{det}$ can be taken from either the output node N3 or the output node N4. Most preferably, the inverters 24, 26, 30, and 32 are CMOS inverters, and the dimensions of the various circuit elements on both sides of the circuit are identical (e.g., the channel length and width of the MOS transistors of the NOR gates 20, 22 are preferably identical, and the channel length and width of the MOS transistors of the inverters 24, 26 and 30, 32 are preferably identical). Further, the NOR gates 20, 22 are most preferably current-biased. However, it should be clearly understood that the specific implementation of the low frequency oscillator 16 is not limiting to the present invention, in its broadest sense.

Figure 3:
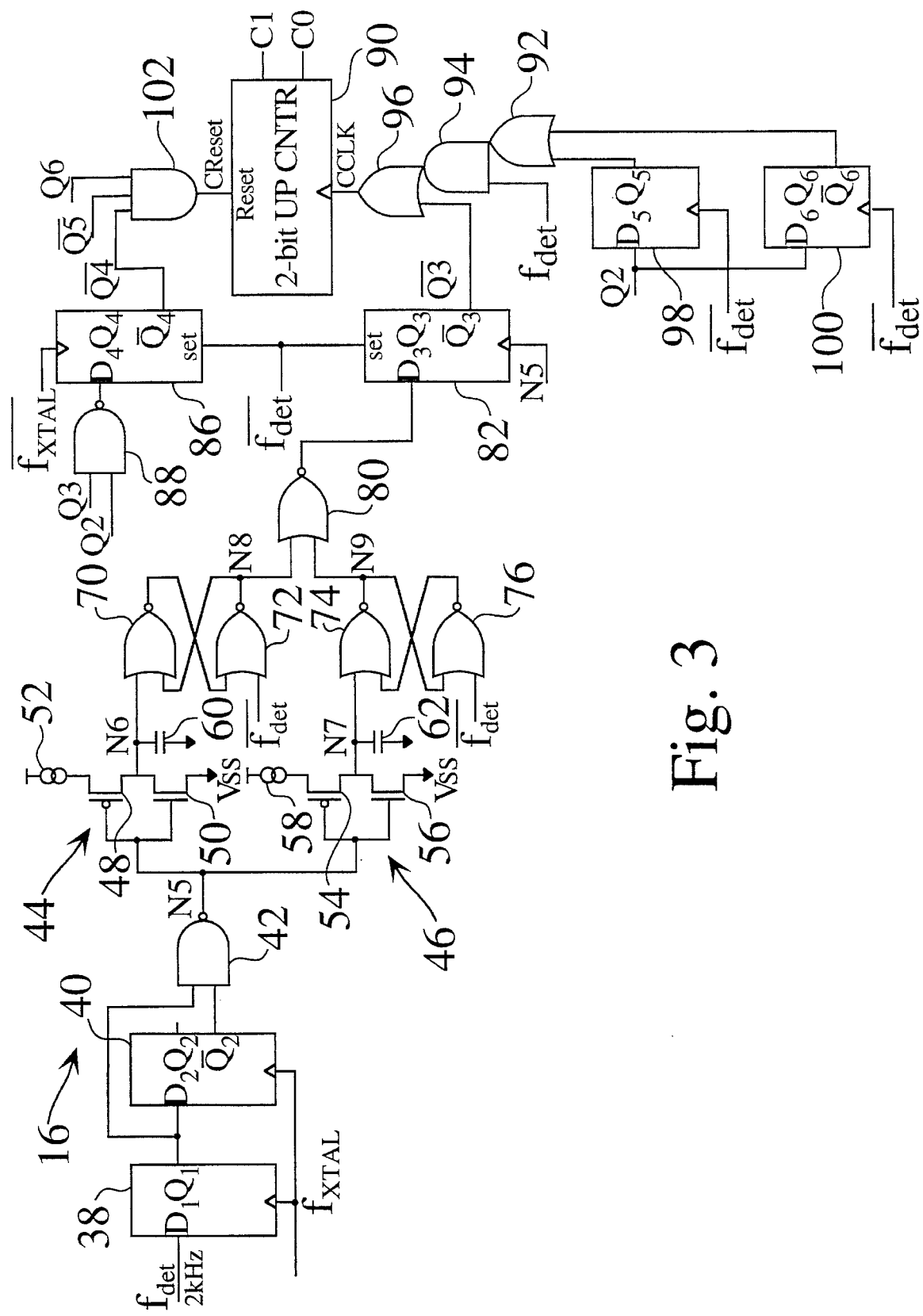
FIG. 3 is a schematic diagram of a presently preferred embodiment of the overspeed/underspeed detector of the fail-safe clock generator of the present invention depicted in FIG. 1.
Figure 4:
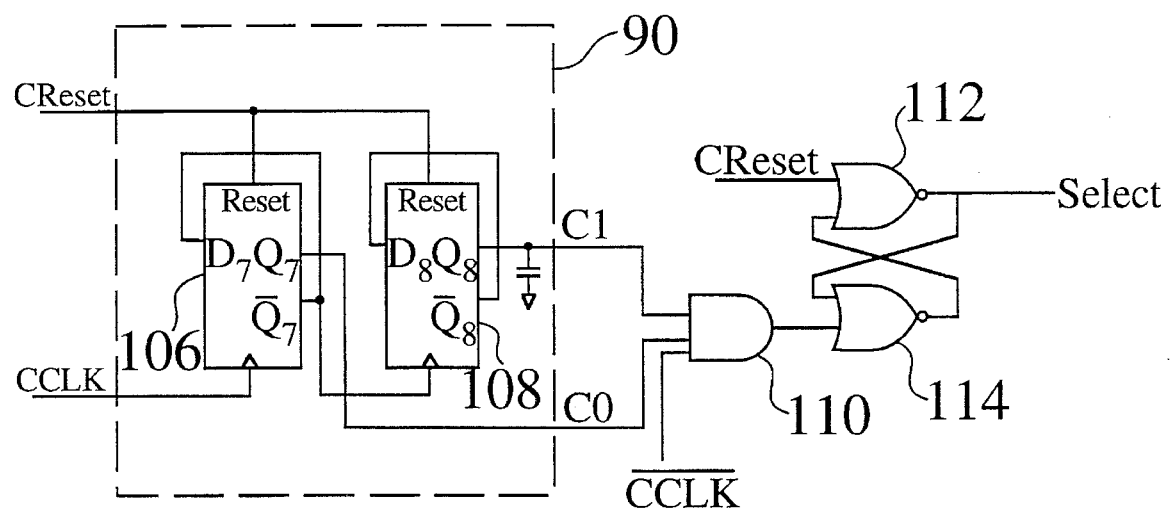
FIG. 4 is a schematic diagram of the back-up mode selector portion of the overspeed/underspeed detector depicted in FIG. 3.

With reference now to FIGS. 3 and 4, in the presently preferred embodiment of the present invention, the overspeed/underspeed detector 16 is implemented as shown. More particularly, with particular reference now to FIG. 3, the overspeed/underspeed detector 16 includes first and second D-type flip-flops 38, 40 which are sequentially connected, with the true output Q1 of the first flip-flop 38 coupled to the data input D2 of the second flip-flop 40. The crystal clock signal $f_{XTL}$ is commonly applied to the clock inputs of the flip-flops 38, 40, and the low frequency clock signal $f_{det}$ is coupled to the data input D1 of the first flip-flop 38. The true output Q1 of the first flip-flop 38 is coupled to a first input of a two-input NAND gate 42, and the complement output/Q2 of the second flip-flop 40 is coupled to the second input of the two-input NAND gate 42.

The overspeed/underspeed detector 16 further includes a first CMOS inverter 44 and a second CMOS inverter 46 configured parallel to one another. The first CMOS inverter 44 is comprised of a PMOS transistor 48 and an NMOS transistor 50 connected in series between a first current source 52 and a reference potential (Vss), such as ground. The second CMOS inverter 46 is comprised of a PMOS transistor 54 and an NMOS transistor 56 connected in series between a second current source 58 and Vss. Preferably, the first and second current sources 52 and 58 are identical, e.g., 100 nA, current sources. The gate electrodes of the PMOS transistor 48 and NMOS transistor 50 of the first CMOS inverter 44, and the gate electrodes of the PMOS transistor 54 and NMOS transistor 56 of the second CMOS inverter 46, are commonly coupled to the output node N5 of the NAND gate 42. A first capacitor 60 is coupled between the output node N6 of the first CMOS inverter 44 and Vss, and a second capacitor 62 is coupled between the output node N7 of the second CMOS inverter 46 and Vss.

The detector 16 further includes a first latch comprised of cross-coupled NOR gates 70, 72, and a second latch comprised of cross-coupled NOR gates 74, 76. The free input of the NOR gate 70 of the first latch is coupled to the output node N6 of the first CMOS inverter 44, and the free input of the NOR gate 72 of the first latch is coupled to the complement (/$f_{det}$) of the low frequency clock signal $f_{det}$. The free input of the NOR gate 74 of the second latch is coupled to the output node N7 of the second CMOS inverter 46, and the free input of the NOR gate 76 of the second latch is also coupled to the complement (/$f_{det}$) of the low frequency clock signal $f_{det}$. The output node N8 of the first latch is coupled to a first input of a two-input NOR gate 80, and the output node N9 of the second latch is coupled to the second input of the NOR gate 80. The output of the NOR gate 80 is coupled to the data input D3 of a third D-type flip-flop 82, whose clock input is coupled to the output "N5" of the NAND gate 42.

The dimensions of the PMOS transistor 48 and the NMOS transistor 50 of the first CMOS inverter 44, and the capacitance of the first capacitor 60 are chosen to introduce a "first latch trip delay" equal to the maximum allowable period ($\tau_{max}$) of the crystal clock signal $f_{XTL}$, and the dimensions of the PMOS transistor 54 and the NMOS transistor 56 of the second CMOS inverter 46, and the capacitance of the second capacitor 62 are chosen to introduce a "second latch trip delay" equal to the minimum allowable period ($\tau_{max}$) of the crystal clock signal $f_{XTL}$. In this regard, the "first latch trip delay" is the time between a transition (e.g., rising edge) of the output "N5" of the NAND gate 42 and the tripping of the first latch, and the "second latch trip delay" is the time between a transition of the output "N5" of the NAND gate 42 and the tripping of the second latch. In actual implementation, with the crystal clock signal $f_{XTL}$ having a frequency of 100 kHz, it is presently contemplated that $\tau_{max}$ will be approximately 11 µs, and that $\tau_{xmin}$ in will be approximately 9 µs, which corresponds to a normal or safe operating range of 91 kHz-110 kHz. In this connection, the PMOS transistor 48 and the NMOS transistor 50 of the first CMOS inverter 44 preferably have greater channel widths than the corresponding channel widths of the PMOS transistor 54 and NMOS transistor 56 of the second CMOS inverter 46, respectively. In actual implementation, it is presently contemplated that the channel width of the PMOS transistor 48 will be 23.2 µm and the channel width of the PMOS transistor 54 will be 16.7 µm, and that the channel width of the NMOS transistor 50 will be 11.6 µm and the channel width of the NMOS transistor 56 will be 8.4 µm. It is presently contemplated that the channel length of each of the transistors 48, 50, 54, 56, will be 1.2 µm.

The detector 16 further includes a fourth D-type flip-flop 86 whose clock input is coupled to the complement (/$f_{XTL}$) of the crystal clock signal $f_{XTL}$, and whose data input D4 is coupled to the output of a two-input NAND gate 88 having a first input coupled to the true output Q3 of the third D-type flip-flop 82, and a second input coupled to the true output Q2 of the second D-type flip-flop 40. The set input of the third and fourth flip-flops 82, 86 are commonly coupled to the complement (/$f_{det}$) of the low frequency clock signal $f_{det}$.

The detector 16 further includes a 2-bit (modulo-4) up counter 90 configured to count the number of consecutive times that the frequency of the crystal clock signal $f_{XTL}$ falls outside of the prescribed normal or safe operating range, e.g., 91 kHz-110 kHz, in a manner to be described hereinafter. When the terminal count (i.e., 4) of the counter 90 is reached, both output bits "C0" and "C1" are at a logic high level (i.e., binary "1").

The detector 16 further includes a gating network comprised of a two-input OR gate 92, a two-input AND gate 94, and a two-input OR gate 96, sequentially arranged in a cascade configuration. A first input of the OR gate 92 is coupled to the true output Q5 of a fifth D-type flip-flop 98, and the second input of the OR gate 92 is coupled to the complement output/Q6 of a sixth D-type flip-flop 100. A first input of the AND gate 94 is coupled to the low frequency clock signal $f_{det}$, and the second input of the AND gate 94 is coupled to the output of the OR gate 92. A first input of the OR gate 96 is coupled to the complement output/Q3 of the third D-type flip-flop 82. The output "CCLK" of the OR gate 96 is coupled to a clock input of the counter 90. The data input D5 of the fifth flip-flop 98, and the data input D6 of the sixth flip-flop 100 are commonly coupled to the true output Q2 of the second flip-flop 40, and the clock input of the fifth and sixth flip-flops 98, 100 are coupled to the complement (/$f_{det}$) of the low frequency clock signal $f_{det}$.

The detector 16 further includes a three-input AND gate 102 having a first input coupled to the complement output/Q4 of the fourth flip-flop 86, a second input coupled to the complement output/Q5 of the fifth flip-flop 98, and a third input coupled to the true output Q6 of the sixth flip-flop 100. The output "CReset" of the AND gate 102 is coupled to a reset input of the counter 90.

With particular reference now to FIG. 4, a presently preferred implementation of the 2-bit up counter 90 and the output stage of the detector 16 will now be described. More particularly, the 2-bit up counter 90 includes a seventh D-type flip-flop 106 and an eighth D-type flip-flop 108. The complement output/Q7 of the seventh flip-flop 106 is commonly coupled to the data input D7 of the seventh flip-flop 106 and to the clock input of the eighth flip-flop 108. The true output Q7 of the seventh flip-flop 106 constitutes the first output bit C0 of the counter 90. The complement output/Q8 of the eighth flip-flop 108 is coupled to the data input D8 of the eighth flip-flop 108, and the true output Q8 of the eighth flip-flop 108 constitutes the second output bit C1 of the counter 90. The reset terminals of the seventh and eighth flip-flops 106, 108 are commonly coupled to the "CReset" output of the AND gate 102. The clock input of the seventh flip-flop 106 is coupled to the "CCLK" output of the OR gate 96.

With continuing reference to FIG. 4, the output stage of the detector 16 includes a three-input AND gate 110 having a first input coupled to the first output bit C0 of the counter 90, a second input coupled to the second output bit C1 of the counter 90, and a third input coupled to the complement/CCLK of the output "CCLK" of the OR gate 96. The output stage of the detector 16 further includes a latch comprised of cross-coupled NOR gates 112, 114. The free input of the NOR gate 112 is coupled to the "CReset" output of the AND gate 102, and the free input of the NOR gate 114 is coupled to the output of the AND gate 110. The output of the NOR gate 112 constitutes the "Select" output of the detector 16.

Figure 5:
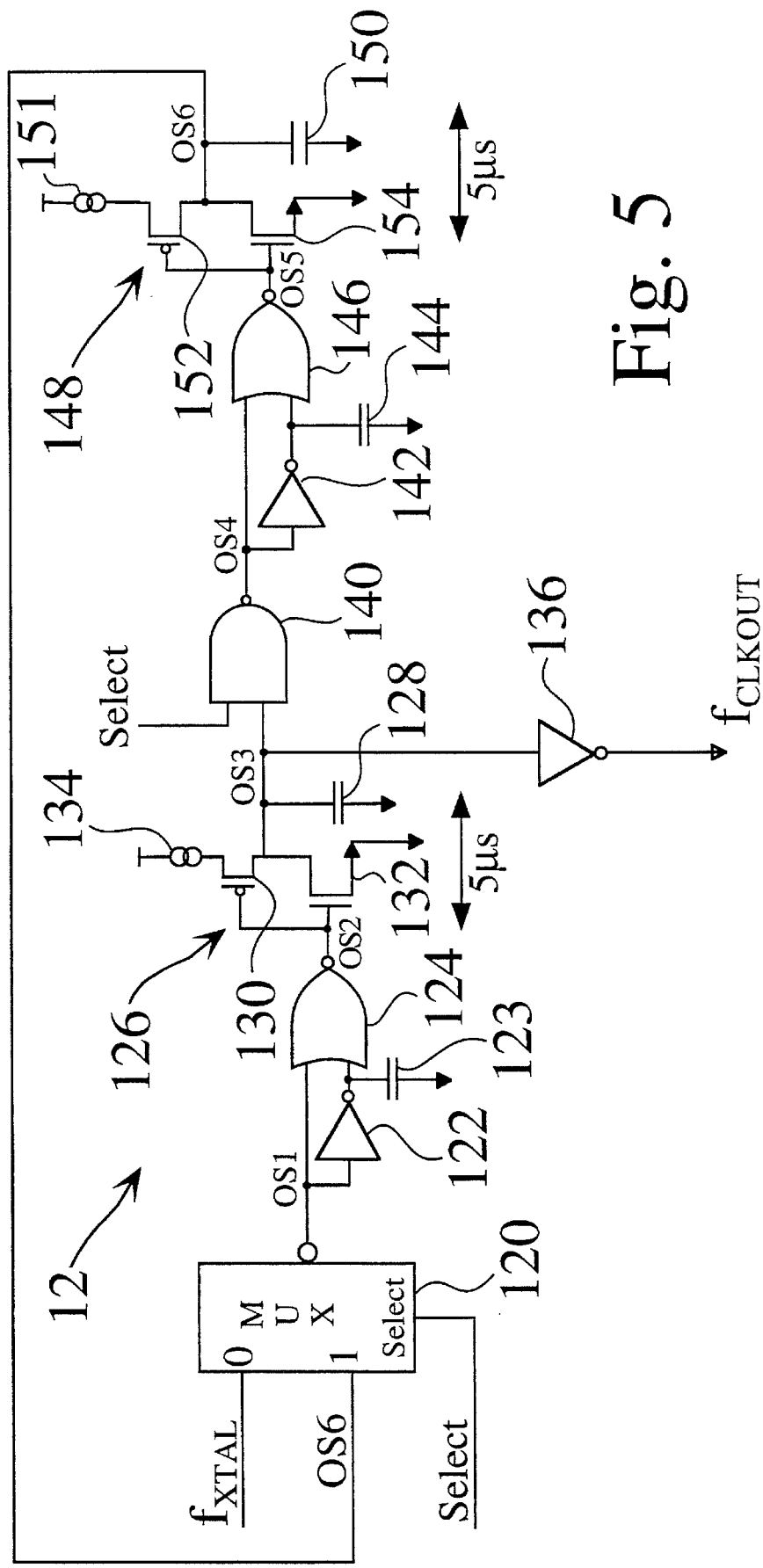
FIG. 5 is a schematic diagram of a presently preferred embodiment of the one-shot generator of the fail-safe clock generator of the present invention depicted in FIG. 1.

With reference now to FIG. 5, in the presently preferred embodiment of the present invention, the one-shot generator 12 is implemented as shown. More particularly, the one-shot generator 12 includes a two-input multiplexer 120 having a first input ("0") coupled to the crystal clock signal $f_{XTL}$, and a second input ("1") coupled to a one-shot trigger pulse "OS6" generated in response to the "Select" output of the detector 16. The select input of the multiplexer 120 is coupled to the "Select" output of the detector 16. Thus, the "Select" output of the detector 16 controls which of the two inputs to the multiplexer 120 is selected. The multiplexer 120 produces an output OS1 which is the inverse of the selected input.

The one-shot generator 12 further includes a first pulse generator comprised of an inverter 122 having its input coupled to the output OS1 of the multiplexer 120, a two-input NOR gate 124 having a first input coupled to the output OS1 of the multiplexer 120, and its second input coupled to the output of the inverter 122, and a capacitor 123 coupled between the output of the inverter 122 and Vss. The first pulse generator produces an output OS2 which consists of a train of very short duration pulses. More particularly, the duration of the pulses generated by the first pulse generator is approximately equivalent to the propagation delay of the inverter 122, which is preferably a CMOS inverter.

The one-shot generator 12 further includes a first sawtooth ramp generator comprised of a CMOS inverter 126 and a capacitor 128. The CMOS inverter 126 includes a PMOS transistor 130 and an NMOS transistor 132 connected in series between a current source 134 and Vss. The gate electrodes of the PMOS transistor 130 and the NMOS transistor 132 are commonly coupled to the output OS2 of the NOR gate 124. The capacitor 128 is coupled between the output node of the CMOS inverter 126 and Vss. Of course, the output OS3 of the first sawtooth ramp generator has a sawtooth waveform.

The one-shot generator 12 further includes an output inverter 136 (preferably a CMOS inverter) having an input coupled to the output OS3 of the first sawtooth ramp generator. The output of the output inverter 136 is the output clock signal $f_{CLKOUT}$. In the presently preferred embodiment of the present invention, the first sawtooth ramp generator is configured in such a manner that the output OS3 thereof reaches the trip point level of the output inverter 136 approximately 5 μs after a charge (ramp) cycle is triggered by the output OS2 of the first pulse generator.

The one-shot generator 12 further includes a two-input NAND gate 140 having a first input coupled to the "Select" output of the overspeed/underspeed detector 16, and a second input coupled to the output OS3 of the first sawtooth ramp generator. The one-shot generator 12 also includes a second pulse generator and a second sawtooth ramp generator which are preferably identical to the first pulse generator and the first sawtooth ramp generator, respectively. More particularly, the second pulse generator is comprised of an inverter 142, a capacitor 144, and a NOR gate 146, configured in the same manner as the corresponding circuit elements of the first pulse generator. The second sawtooth ramp generator is comprised of a CMOS inverter 148 and a capacitor 150 configured in the same manner as the corresponding circuit elements of the first sawtooth ramp generator. The CMOS inverter 148 is comprised of a PMOS transistor 152 and an NMOS transistor 154 connected in series between a current source 151 and Vss.

The output OS4 of the NAND gate 140 is applied as an input to the inverter 142 and the NOR gate 146. The output OS5 of the NOR gate 146 is applied as an input to the gate electrodes of the PMOS and NMOS transistors 152, 154 of the CMOS inverter 148. The output OS6 of the CMOS inverter 148 is applied to the "1" input of the multiplexer.

With reference now to FIGS. 3–5, and additional reference to the timing diagrams depicted in FIGS. 6 and 7, the operation of the above-described crystal oscillator and back-up circuit of the presently preferred embodiment of the present invention will now be described.

Figure 6:
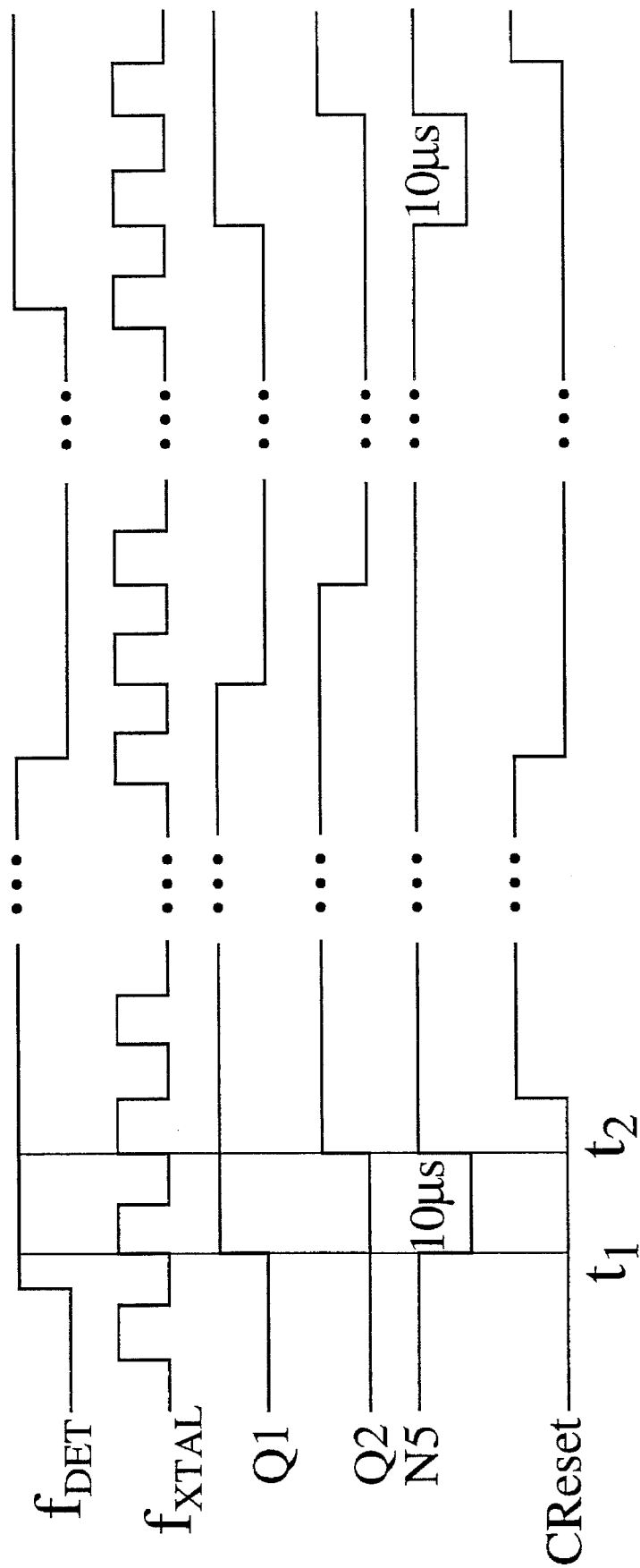
FIG. 6 is a timing diagram illustrating the operation of the overspeed/underspeed detector depicted in FIG. 3.
Figure 7:
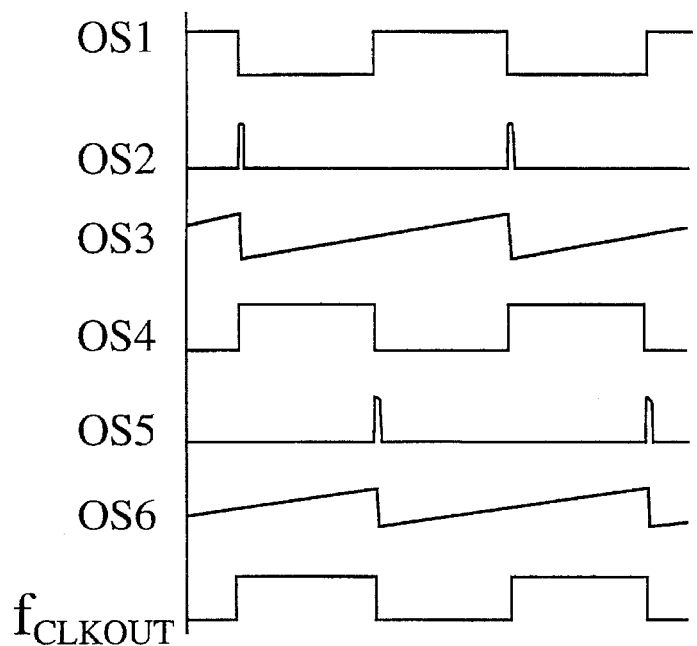
FIG. 7 is a timing diagram illustrating the operation of the one-shot generator depicted in FIG. 5; and, FIG. 8 is a partial schematic diagram of an alternative embodiment of the back-up mode selector portion of the overspeed/underspeed detector depicted in FIG. 4.

With particular reference initially to FIGS. 3 and 6, the low frequency clock signal $f_{det}$ is synchronized to the crystal clock signal $f_{XTL}$ in the following manner. Namely, since $f_{det}$ is applied to the data input D1 of the first flip-flop 38 of the detector 16, and $f_{XTL}$ is applied to the clock input of the first flip-flop 38, then the true output Q1 of the first flip-flop 38 goes high in response to the rising edge of the first $f_{XTL}$ pulse which occurs after $f_{det}$ goes high, as depicted by the vertical time line t1 in FIG. 6. The output "N5" of the NAND gate 42 goes low in response to the rising edge of Q1, since both inputs (Q1 and /Q2) to the NAND gate 42 are high at this time (t1). The complement output /Q2 of the second flip-flop 40 is high until the rising edge of the next $f_{XTL}$ pulse, at which time, t2, "N5" goes high. Thus, "N5" is a pulse whose width is equal to the duration of the window (t2-t1) between the rising edge of Q1 and the rising edge of Q2 (or falling edge of /Q2), which, in turn, is equal to the period $\tau_x$ of $f_{XTL}$. Thus, if the frequency of $f_{XTL}$ is 100 kHz, $\tau_x$ (and the pulse width of "N5")=10 μs.

If the frequency of $f_{XTL}$ is within its prescribed normal or safe operating range of 91 kHz–110 kHz, i.e., if $\tau_x$ is within the range of 9 μs–11 μs, then the second latch comprised of the cross-coupled NOR gates 74, 76 is tripped, thus causing the output of the NOR gate 80, which is coupled to the data input D3 of the third flip-flop 82, to go high, and the complement output /Q3 of the third flip-flop 82 to go low.

Thus, in a normal mode of operation, the complement output /Q3 of the third flip-flop 82 will always be low. More particularly, when the actual value of $\tau_x$ is within the range of 9 μs–11 μs, then $\tau_{min} < \tau_x < \tau_{max}$, so that $\tau_x$ is greater than the "second latch trip delay", but less than the "first latch trip delay". Consequently, the output node N7 of the second CMOS inverter 46 is high, and the output node N9 of the second latch is low. Since both inputs to the NOR gate 70 of the first latch are low at this time, then the output of the NOR gate 70, which is coupled to the input of the NOR gate 72 of the first latch, is high. Consequently, the output node N8 of the first latch is low. As such, both inputs to the NOR gate 80 are low, and thus, the output of the NOR gate 80 is high, and /Q3 is low.

However, if the actual value of $\tau_x$ is either greater than $\tau_{max}$, or less than $\tau_{min}$, then the output of the NOR gate 80 will go low, and thus, /Q3 will go high. More particularly, if the actual value of $\tau_x$ is less than $\tau_{min}$, then the output node N7 of the second CMOS inverter 46 will go low, and thus, the output of the NOR gate 74, i.e., the output node N9 of the second latch, will go high. Consequently, the output of the NOR gate 80 will go low, and thus, /Q3 will go high. If the actual value of $\tau_x$ is greater than $\tau_{max}$, then the output node N6 of the first CMOS inverter 44 will go high, and the output of the NOR gate 70 of the first latch will go low. Consequently, the output of the NOR gate 72, i.e., the output node N8 of the first latch, will go high. Thus, the output of the NOR gate 80 will go low, and thus, /Q3 will go high.

Thus, in operation, /Q3 goes high when the frequency of $f_{XTL}$ falls outside of its prescribed normal or safe operating range of 91 kHz-110 kHz (i.e., when $\tau_x$ is outside of the range of 9 μs-11 μs). Thus, the logic level of /Q3 is indicative of whether an overspeed or underspeed failure of the crystal oscillator 10 has occurred during a given cycle of $f_{det}$. When an overspeed or underspeed failure of the crystal oscillator 10 occurs, /Q3 goes high, as previously explained, and thus, the output "CCLK" of the OR gate 96 goes high, thus clocking or incrementing the 2-bit up counter 90. If four consecutive overspeed and/or underspeed failures of the crystal oscillator 10 occur (i.e., if /Q3 goes high during four consecutive cycles of $f_{det}$), then the up counter 90 will have reached its terminal count (i.e., 4), whereby both output bits, C0 and C1, of the counter 90 will be high. When C0 and C1 are both high, the output of the AND gate 110 of the output stage of the detector 16 goes high, and the output of the NOR gate 114 goes low. At this time, the "CReset" output of the AND gate 102 is low (because /Q4 is low), and thus, the "Select" output of the detector 16 goes high. However, if the "CReset" output of the AND gate 102 goes high before the counter 90 counts up to its terminal count, then the counter 90 is reset, i.e., the output bits C0 and C1 of the flip-flops 106 and 108 of the counter 90 are forced to zero, and thus, the counter 90 is re-initialized (cleared) to begin counting over from zero.

With reference now to FIG. 5, in response to the "Select" output of the detector 16 going high, the input of the multiplexer 120 of the one-shot generator 12 is switched from its first input ("0") to its second input ("1"), i.e., the back-up mode of operation is initiated, whereby the control of the one-shot generator 12 is taken over from the crystal oscillator 10 by the back-up circuit comprised of the low frequency oscillator 14 and the overspeed/underspeed detector 16. More particularly, with additional reference now to FIG. 7, when the "Select" output of the detector 16 goes high, the NAND gate 140 is enabled, i.e., its output OS4 is enabled to go from its normal high logic level to a low logic level upon OS3 reaching the logic threshold voltage level of the NAND gate 140. In response to OS4 going low, the second pulse generator of the one-shot generator 12 generates a pulse OS5, which, in turn, triggers the second sawtooth ramp generator of the one-shot generator 12 to produce the OS6 one-shot trigger signal having a sawtooth waveform. The one-shot trigger signal OS6 is applied to the "1" input of the multiplexer 120, which was selected by the "Select" output of the detector 16. As long as the "Select" output of the detector 16 is high, i.e., until the "CReset" output of the AND gate 102 of the detector 16 goes high, the one-shot generator 12 is responsive to the one-shot trigger signal OS6 to generate the clock output signal $f_{CLKOUT}$ (i.e., the one-shot generator 12 is in a "self-clocking mode of operation").

With additional reference now to FIGS. 3 and 6, during any given cycle of $f_{det}$, if the frequency of $f_{XTL}$ is within its safe operating range (i.e., 91 kHz-110 kHz), then /Q3 is low, and thus, Q3 is high. Additionally, since Q2 goes high on the rising edge of "N5", then the output of the NAND gate 88 goes low, and the complement output /Q4 of the fourth flip-flop 86 goes high. Further, since /Q5 and Q6 are high at all times that the crystal oscillator 10 is operative (i.e., Q5 and Q6 are high unless the crystal oscillator 10 stops or $f_{XTL}<f_{det}$ (i.e., 2 kHz)), then the "CReset" output of the AND gate 102 goes high when the frequency of $f_{XTL}$ is within its safe operating range. As such, the 2-bit up counter 90 is reset and the "Select" output of the detector 16 goes low whenever "CReset" goes high.

If "CReset" goes high before four consecutive overspeed and/or underspeed failures of the crystal oscillator 10 are detected by the detector, then the counter 90 is reset, i.e., the output bits C0 and C1 of the flip-flops 106 and 108 of the counter 90 are forced to zero, and thus, the counter 90 is re-initialized to begin counting over from zero. In this case, the counter 90 does not reach its terminal count, and thus, the "Select" output of the detector 16 does not go high. Consequently, the operation of the one-shot generator 12 remains under the control of the crystal oscillator 10, i.e., a normal mode of operation is maintained.

If the crystal oscillator 10 recovers normal operation while the one-shot generator 12 is under the control of the back-up circuit (i.e., during a back-up mode of operation), then "CReset" goes high, and thus, the 2-bit up counter 90 is reset and the "Select" output of the detector 16 goes low, thereby switching the input of the multiplexer 120 of the one-shot generator 12 back from it second input ("1") to its first input ("0"), whereby the control of the one-shot generator 12 is taken over from the back-up circuit by the crystal oscillator 10, i.e., the system returns to its normal mode of operation.

Figure 8:
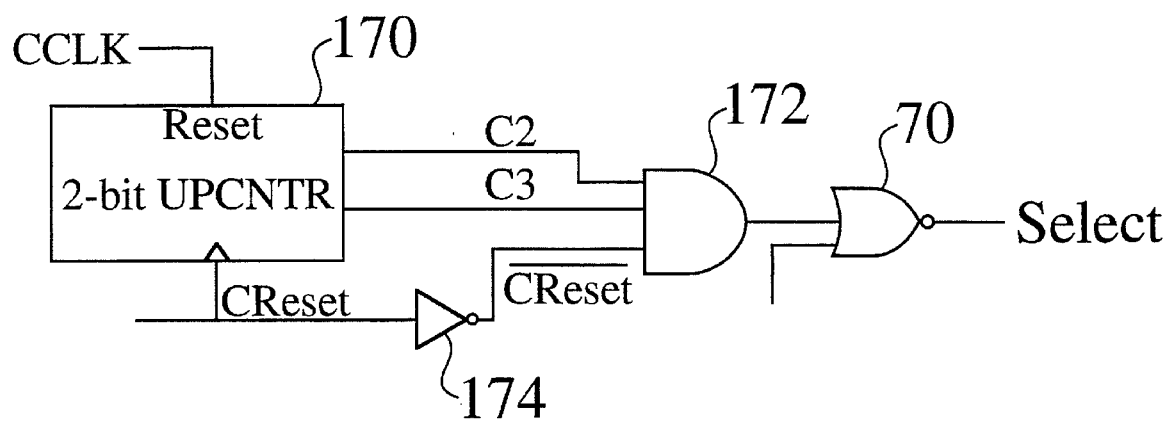

However, with reference now to FIG. 8, in accordance with an alternative embodiment of the present invention, the detector 16 is provided with an additional 2-bit up counter 170 having a reset input coupled to "CCLK", and a clock input coupled to "CReset". The output bits C2 and C3 of the up counter 170 are applied as first and second inputs of a three-input AND gate 172. The third input of the AND gate 172 is coupled to the output "/CReset" of an inverter 174 whose input is coupled to "CReset". The output "CReset2" of the AND gate 172 is coupled to the free input of the NOR gate 70, instead of "CReset" being coupled to the free input of the NOR gate 70, as in the primary embodiment of the present invention. With this alternative embodiment of the present invention, the frequency of $f_{XTL}$ must fall within its safe operating range during four consecutive cycles of $f_{det}$ before the "Select" output of the detector 16 is allowed to go low (i.e., before the system is allowed to return to its normal mode of operation), thereby switching the input of the multiplexer 120 of the one-shot generator 12 back from it second input ("1") to its first input ("0"), whereby the control of the one-shot generator 12 is taken over from the back-up circuit by the crystal oscillator 10.

Although a presently preferred embodiment of the present invention has been described in detail hereinabove, it should be clearly understood that many variations and/or modifications of the basic inventive concepts herein taught which may appear to those skilled in the pertinent art will still fall within the spirit and scope of the present invention as defined in the appended claims.

What is claimed is:

1. A fail-safe clock generator, comprising:

a primary oscillator for generating a primary clock signal;

a back-up oscillator for generating a back-up clock signal;

a low frequency oscillator for generating a low frequency clock signal having a frequency less than the frequency of said primary clock signal;

an overspeed and underspeed detector coupled to said primary clock signal and responsive to said low frequency clock signal for detecting an overspeed failure of said primary oscillator in response to said primary clock signal exceeding a prescribed maximum frequency over a prescribed plural number of cycles of said low frequency clock signal, and for detecting an underspeed failure of said primary oscillator in response to said primary clock signal falling below a prescribed minimum frequency over a prescribed plural number of cycles of said low frequency clock signal; and, generator output control circuitry for substituting said back-up clock signal in place of said primary clock signal as an output of the generator in response to detection of either overspeed or underspeed failure of said primary oscillator.

2. The clock generator as set forth in claim 1, wherein said primary oscillator comprises a crystal oscillator, whereby said primary clock signal comprises a crystal clock signal.

3. The clock generator as set forth in claim 1, further comprising:

means for switching said output of the generator from said back-up clock signal to said primary clock signal in response to detection of normal operation of said primary oscillator while in a back-up mode of operation in which said back-up clock signal is substituted for said primary clock signal as said output of the generator.

4. A fail-safe clock generator, comprising:

a crystal oscillator for generating a crystal clock signal;

a back-up circuit coupled to said crystal clock signal for detecting an overspeed failure mode in which the frequency of said crystal clock signal exceeds a prescribed maximum frequency for greater than a predetermined time period, and for detecting an underspeed failure mode in which the frequency of said crystal clock signal falls below a prescribed minimum frequency for greater than said predetermined time period, and for generating a back-up mode control signal in response to detection of either said overspeed or underspeed failure mode; and, an output clock generator responsive to said crystal clock signal, during a normal mode of operation, for generating an output clock signal, and responsive to said back-up mode control signal, during a back-up mode of operation, for generating said output clock signal.

5. The clock generator as set forth in claim 4, wherein said back-up circuit comprises:

a low frequency oscillator for generating a low frequency clock signal having a frequency less than the frequency of said crystal clock signal; and, an overspeed/underspeed detector responsive to said low frequency clock signal for detecting the frequency of said crystal clock signal during each period of said low frequency clock signal, and for generating said back-up mode control signal in response to detection of either said overspeed or underspeed failure mode, wherein said predetermined time period comprises a plurality of consecutive periods of said low frequency clock signal.

6. The clock generator as set forth in claim 5, further comprising means for disabling said back-up mode control signal in response to non-detection of either said overspeed or underspeed failure mode over a plurality of consecutive periods of said low frequency clock signal.

7. The clock generator as set forth in claim 4, wherein said output clock generator comprises a one-shot clock generator.

8. The clock generator as set forth in claim 7, wherein said one-shot generator includes:

circuitry enabled by said back-up mode control signal for generating a one-shot trigger signal;

a multiplexer having a first input coupled to said crystal clock signal, a second input coupled to said one-shot trigger signal, a select input responsive to said back-up mode control signal for selecting said second input, during said back-up mode of operation, and an output; and, circuitry responsive to said output of said multiplexer for generating said output clock signal.

9. The clock generator as set forth in claim 5, wherein said overspeed/underspeed detector comprises:

a first circuit portion for detecting either said overspeed or underspeed failure mode during each period of said low frequency clock signal, and for generating a counter clock signal in response to each detection of said overspeed or underspeed failure mode;

a second circuit portion for generating a counter reset signal in response to non-detection of said overspeed or underspeed failure mode during each period of said low frequency clock signal;

a counter having a clock input coupled to said counter clock signal, a reset input coupled to said counter reset signal, and a plurality of outputs, said counter being incremented in response to said counter clock signal and reset in response to said counter reset signal; and, a third circuit portion coupled to said outputs of said counter for generating said back-up mode control signal in response to said counter reaching its terminal count.

10. The clock generator as set forth in claim 9, wherein said first circuit portion comprises:

a pulse generator coupled to said low frequency clock signal and said crystal clock signal for generating a window pulse having a width equal to the actual period of said crystal clock signal during each period of said low frequency clock signal;

first delay means for generating a first logic control signal in response to said actual period of said crystal clock signal exceeding a prescribed maximum period;

second delay means for generating a second logic control signal in response to said actual period of said crystal clock signal falling below a prescribed minimum period; and, logic circuitry responsive to either said first logic control signal or said second logic control signal for generating said counter clock signal.

11. The clock generator as set forth in claim 9, wherein said first circuit portion comprises:

a first flip-flop having a data input coupled to said low frequency clock signal, a clock input coupled to said crystal clock signal, and a true output;

a second flip-flop having a data input coupled to said true output of said first flip-flop, a clock input coupled to said crystal clock signal, a true output, and a complement output;

a first NAND gate having a first input coupled to said true output of said first flip-flop, a second output coupled to said complement output of said second flip-flop, and an output having a low logic level between consecutive rising edges of said crystal clock signal, and a high logic level at all other times;

first delay circuitry coupled to said output of said first NAND gate for producing a first gate control signal having a high logic level when said output of said first NAND gate is at said low logic level for greater than a prescribed maximum period of said crystal clock signal, and a low logic level at all other times;

second delay circuitry coupled to said first NAND gate for producing a second gate control signal having a high logic level when said output of said first NAND gate is at said low logic level for greater than a prescribed minimum period of said crystal clock signal, and a low logic level at all other times;

a first latch coupled to said first gate control signal for generating a first latch output signal having a high logic level when said first gate control signal is at said high logic level, and a low logic level at all other times;

a second latch coupled to said second gate control signal for generating a second latch output signal having a high logic level when said second gate control signal is at said low logic level, and a low logic level at all other times;

a NOR gate having a first input coupled to said first latch output signal, a second input coupled to said second latch output signal, and an output;

a third flip-flop having a data input coupled to said output of said NOR gate, a clock input coupled to said output of said first NAND gate, a set input coupled to a complement low frequency clock signal which is the complement of said low frequency clock signal, a true output, and a complement output; and, a first OR gate having a first input coupled to said complement output of said third flip-flop, a second input, and an output, wherein said output of said first OR gate is said counter clock signal.

12. The clock generator as set forth in claim 11, wherein:

said first delay circuitry comprises a first CMOS inverter comprised of a first PMOS transistor and a first NMOS transistor connected in series between a first current source and a reference potential, and a first capacitor coupled between an output node of said first CMOS inverter and said reference potential; and, said second delay circuitry comprises a second CMOS inverter comprised of a first PMOS transistor and a first NMOS transistor connected in series between a second current source and said reference potential, and a second capacitor coupled between an output node of said second CMOS inverter and said reference potential.

13. The clock generator as set forth in claim 12, wherein:

said first latch is comprised of first and second cross-coupled NOR gates, said first one of cross-coupled NOR gates having a free input coupled to said first gate control signal, and said second one of said cross-coupled NOR gates having a free input coupled to said complement back-up signal; and, said second latch is comprised of third and fourth cross-coupled NOR gates, said third one of said cross-coupled NOR gates having a free input coupled to said second gate control signal, and said fourth one of said cross-coupled NOR gates having a free input coupled to said complement low frequency clock signal.

14. The clock generator as set forth in claim 11, wherein said second circuit portion comprises:

a second NAND gate having a first input coupled to said true output of said second flip-flop, a second input coupled to said true output of said third flip-flop, and an output;

a fourth flip-flop having a data input coupled to said output of said second NAND gate, a clock input coupled to a complement crystal clock signal which is the complement of said crystal clock signal, a set input coupled to said complement low frequency clock signal, a true output, and a complement output; and, a counter reset signal generator coupled to said complement output of said fourth flip-flop for generating said counter reset signal.

15. The clock generator as set forth in claim 14, further comprising catastrophic crystal failure means for generating said counter clock signal during each period of said low frequency clock signal when the frequency of said crystal clock signal is less than the frequency of said low frequency clock signal.

16. The clock generator as set forth in claim 15, wherein said catastrophic crystal failure means comprises:

a fifth flip-flop having a first input coupled to said true output of said second flip-flop, a clock input coupled to said complement low frequency clock signal, a true output, and a complement output;

a sixth flip-flop having a first input coupled to said true output of said second flip-flop, a clock input coupled to said complement low frequency clock signal, a true output, and a complement output;

a second OR gate having a first input coupled to said true output of said fifth flip-flop, a second input coupled to said complement output of said sixth flip-flop, and an output;

a first AND gate having a first input coupled to said low frequency clock signal, a second input coupled to said output of said second OR gate, and an output; and, wherein said output of said first AND gate is coupled to said second input of said first OR gate.

17. The clock generator as set forth in claim 16, wherein said reset counter signal generator comprises a second AND gate having a first input coupled to said complement output of said fourth flip-flop, a second input coupled to said complement output of said fifth flip-flop, a third input coupled to said true output of said sixth flip-flop, and an output, wherein said output of said second AND gate is said counter reset signal.

18. A fail-safe clock generator, comprising:

a crystal oscillator for generating a crystal clock signal;

detecting means coupled to said crystal clock signal for detecting an overspeed failure mode in which the frequency of said crystal clock signal exceeds a prescribed maximum frequency for greater than a predetermined time period and for detecting an underspeed failure mode in which the frequency of said crystal clock signal falls below a prescribed minimum frequency for greater than said predetermined time period, and for generating a back-up mode control signal in response to detection of either said overspeed or underspeed failure mode; and, means responsive to said crystal clock signal, during a normal mode of operation, for generating an output clock signal, and responsive to said back-up mode control signal, during a back-up mode of operation, for generating said output clock signal.

19. The clock generator as set forth in claim 18, wherein said detecting means comprises:

a low frequency oscillator for generating a low frequency clock signal having a frequency less than the frequency of said crystal clock signal; and, means responsive to said low frequency clock signal for detecting the frequency of said crystal clock signal during each period of said low frequency clock signal, and for generating said back-up mode control signal in response to detection of either said overspeed or underspeed failure mode.

20. The clock generator as set forth in claim 18, wherein said detecting means comprises:

a low frequency oscillator for generating a low frequency clock signal having a frequency less than the frequency of said crystal clock signal; and, means responsive to said low frequency clock signal for detecting the frequency of said crystal clock signal during each period of said low frequency clock signal, and for generating said back-up mode control signal in response to detection of either said overspeed or underspeed failure mode, wherein said predetermined time period comprises a plurality of consecutive periods of said low frequency clock signal.

21. The clock generator as set forth in claim 20, wherein said means for generating an output clock signal comprises a one-shot generator.

22. The clock generator as set forth in claim 21, wherein said one-shot generator includes:

means enabled by said back-up mode control signal for generating a one-shot trigger signal;

a multiplexer having a first input coupled to said crystal clock signal, a second input coupled to said one-shot trigger signal, a select input responsive to said back-up mode control signal for selecting said second input, during said back-up mode of operation, and an output; and, means responsive to said output of said multiplexer for generating said output clock signal.

23. A method for generating an output clock signal, including the steps of:

generating a primary clock signal;

generating a back-up clock signal;

detecting whether the frequency of said primary clock signal is greater than a prescribed maximum frequency for greater than a predetermined time period and detecting whether the frequency of said primary clock signal is less than a prescribed minimum frequency for greater than said predetermined time period; and, applying said primary clock signal as the output clock signal during a normal mode of operation, and applying said back-up clock signal as the output clock signal in response to detection that the frequency of said primary clock signal is greater than said prescribed maximum frequency for greater than said predetermined time period or less than said prescribed minimum frequency for greater than said predetermined time period.

24. A method for generating an output clock signal, including the steps of:

generating a crystal clock signal;

generating a back-up clock signal having a frequency lower than that of said crystal clock signal;

determining whether the frequency of said crystal clock signal is greater than a prescribed maximum frequency or less than a prescribed minimum frequency;

generating a control signal in response to the frequency of said crystal clock signal being greater than said prescribed maximum frequency or less than said prescribed minimum frequency over a predetermined time period; and, applying said control signal to a one-shot generator to switch said one-shot generator from a normal mode of operation in which said one-shot generator is responsive to said crystal clock signal for generating said output clock signal, to a back-up mode of operation in which said one-shot generator operates in a self-clocking mode to generate said output clock signal.

25. The method as set forth in claim 24, wherein said predetermined time period constitutes a predetermined number of consecutive cycles of said low frequency clock signal.

26. The method as set forth in claim 24, further comprising the step of switching said one-shot generator from said back-up mode of operation to said normal mode of operation in response to the frequency of said crystal clock signal being within its normal operating frequency range over a predetermined number of consecutive periods of said low frequency clock signal.

27. The method as set forth in claim 26, wherein said predetermined number is $\geq 2$.

\* \* \* \* \*